(12) United States Patent
Erhardt et al.

(10) Patent No.: US 9,176,372 B2
(45) Date of Patent: *Nov. 3, 2015

(54) X-RAY DEVICE AND X-RAY SENSITIVE CAMERA FOR PANORAMIC TOMOGRAPHY AND 3D SHOTS

(75) Inventors: Norbert Erhardt, Worms (DE); Werner Gunther, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 412 days.

This patent is subject to a terminal disclaimer.

(21) Appl. No.: 13/438,449

(22) Filed: Apr. 3, 2012

(65) Prior Publication Data

US 2012/0189096 A1    Jul. 26, 2012

Related U.S. Application Data

(63) Continuation of application No. 12/857,254, filed on Aug. 16, 2010, now Pat. No. 8,152,373, which is a continuation of application No. 10/550,600, filed as application No. PCT/DE2004/000620 on Mar. 24, 2004, now Pat. No. 7,798,708.

(30) Foreign Application Priority Data

Mar. 24, 2003  (DE) .................. 103 13 110

(51) Int. Cl.
   *A61B 6/14*  (2006.01)
   *G03B 42/04* (2006.01)
   (Continued)

(52) U.S. Cl.
   CPC .............. *G03B 42/042* (2013.01); *A61B 6/032* (2013.01); *A61B 6/035* (2013.01); *A61B 6/14* (2013.01);
   (Continued)

(58) Field of Classification Search
   CPC .......... A61B 6/14; A61B 6/032; A61B 6/035; A61B 6/4233; A61B 6/4283; A61B 6/501; G01N 23/046; H05G 1/60; H05G 1/64; G01T 1/2018; G01T 1/24; G01T 1/2928
   USPC ......... 378/38–40, 98.8, 189, 191; 250/370.09
   See application file for complete search history.

(56) References Cited

U.S. PATENT DOCUMENTS 4,847,881 A  7/1989 Heubeck
5,058,147 A  10/1991 Nishikawa et al.
(Continued)

FOREIGN PATENT DOCUMENTS

| JP | 09-135829 A | 5/1997 |
| JP | 11-009579 A | 1/1999 |
| WO | 02052505 A2 | 7/2002 |

*Primary Examiner* — Allen C. Ho
(74) *Attorney, Agent, or Firm* — Fitzpatrick, Cella, Harper & Scinto

(57) ABSTRACT

The invention relates to an X-ray device comprising an x-ray sensitive camera for creating tomograms, especially panoramic tomograms. Means for creating 3D shots of a partial volume of the mandibular arch are also provided, said 3D shots being created especially by a second image receiver for creating a 2D shot and means for taking a plurality of 2D shots from different directions and creating a 3D shot therefrom, preferably according to conebeam technology with the associated reconstruction algorithms. The x-ray sensitive camera comprises a first x-ray sensitive image receiver for creating a tomogram, and a second x-ray sensitive image receiver for creating plane shots.

10 Claims, 6 Drawing Sheets

(51) Int. Cl.
*A61B 6/00* (2006.01)
*A61B 6/03* (2006.01)
*G01T 1/29* (2006.01)
*G01T 1/24* (2006.01)
*H04N 5/32* (2006.01)

(52) U.S. Cl.
CPC ............. *A61B 6/4233* (2013.01); *A61B 6/4283* (2013.01); *A61B 6/466* (2013.01); *G01T 1/24* (2013.01); *G01T 1/2928* (2013.01); *H04N 5/32* (2013.01)
USPC ................ 378/40; 378/38; 378/39; 378/98.8; 378/189; 378/191; 250/370.09

(56) References Cited

U.S. PATENT DOCUMENTS

| | | |
|---|---|---|
| 5,257,183 A | 10/1993 | Tam |
| 5,511,106 A | 4/1996 | Doebert et al. |
| 5,579,366 A | 11/1996 | Doebert et al. |
| 6,049,584 A | 4/2000 | Pfeiffer |
| 6,055,292 A | 4/2000 | Zeller et al. |
| 6,118,842 A | 9/2000 | Arai et al. |
| 6,151,382 A | 11/2000 | Gilblom |
| 6,289,074 B1 | 9/2001 | Arai et al. |
| 6,292,530 B1 | 9/2001 | Yavus et al. |
| 6,379,041 B1 | 4/2002 | Schuetz et al. |
| 6,442,238 B2 | 8/2002 | Meulenbrugge |
| 6,466,641 B1 | 10/2002 | Virta et al. |
| 6,493,415 B1 | 12/2002 | Arai et al. |
| 6,574,297 B2 | 6/2003 | Tam |
| 6,584,171 B2 | 6/2003 | Suzuki et al. |
| 6,678,346 B2 | 1/2004 | Hsieh |
| 6,785,360 B1 * | 8/2004 | Annis .......................... 378/137 |
| 7,092,483 B2 | 8/2006 | Nyholm |
| 7,099,428 B2 | 8/2006 | Clinthorne et al. |
| 7,103,141 B2 | 9/2006 | Sonobe et al. |
| 7,197,109 B2 | 3/2007 | Rotondo et al. |
| 7,236,563 B2 * | 6/2007 | Sa et al. ......................... 378/39 |
| 7,315,608 B2 | 1/2008 | Sa et al. |
| 7,322,746 B2 | 1/2008 | Beckhaus et al. |
| 7,405,406 B1 | 7/2008 | Nagarkar et al. |
| 7,470,914 B2 | 12/2008 | Li et al. |
| 7,798,708 B2 * | 9/2010 | Erhardt et al. ................ 378/191 |
| 8,152,373 B2 * | 4/2012 | Erhardt et al. ................ 378/191 |
| 2003/0030721 A1 | 2/2003 | Nyholm |
| 2003/0072406 A1 | 4/2003 | Yang |
| 2003/0210814 A1 | 11/2003 | Nelson |

* cited by examiner

X-RAY DEVICE AND X-RAY SENSITIVE CAMERA FOR PANORAMIC TOMOGRAPHY AND 3D SHOTS

CROSS REFERENCE TO RELATED APPLICATIONS

This application is a continuation of U.S. patent application Ser. No. 12/857,254, filed Aug. 16, 2010, now U.S. Pat. No. 8,152,373, which is a continuation of U.S. patent application Ser. No. 10/550,600, filed Sep. 23, 2005, now U.S. Pat. No. 7,798,708, which is a national phase filing under 35 U.S.C. 371 based on International Application No. PCT/DE04/00620, filed Mar. 24, 2004, which claims the benefit of priority of German Application No. DE 103 13 110.8, filed Mar. 24, 2003, each of which is incorporated by reference herein in its entirety, as if set forth fully herein.

BACKGROUND OF THE INVENTION

Field of the Invention

1. Technical Field

The invention relates to an X-ray system including an X-ray sensitive camera comprising an X-ray sensitive image detector for the creation of a tomographic image, and to a camera used for this purpose.

Such an X-ray system is used to produce dental panoramic tomographic images.

2. Description of the Related Art

A dental X-ray diagnostic device for producing panoramic tomographic images of a patient's jaw is disclosed in EP 0 229 971. In addition to panoramic tomographic images (PAN images), images of one or more user-defined, selectable jaw sections can be produced in a plurality of superposed layers (multilayer images). Furthermore, a film cassette holder is mounted on a rotatable unit bearing the X-ray emitter so that it can be pivoted from an operating position to a non-operating position, which makes it possible to produce teleradiographic images (ceph images), as the X-ray emitter can then direct a beam unhindered past the film cassette holder.

An X-ray diagnostic device for the production of X-ray images of parts of a patient's body is disclosed in EP 0 632 994 A1, in which there is provided a line detector camera with an X-ray detector, the width of which corresponds to the width or the length of the body part to be imaged. The line detector camera can be moved together with the X-ray source along the part of the body to be imaged via regulating means. The X-ray diagnostic device can thus be configured to produce a PAN image as well as a teleradiographic image (ceph image), and the line detector camera for producing the required image can be unplugged and replugged, for which purpose it is equipped with a connector containing connecting means for a detachable mechanical and electrical connection with a holder. Furthermore, various possibilities are disclosed for aiming the X-ray fan beam when producing the teleradiographic image using a movable emitter or a primary diaphragm or a combination of the two.

A camera that is capable of being unplugged and replugged is described in detail in EP 0 634 671 A1, particular attention being paid to the detachable mounting of the camera on a holder.

A detector system for the production of X-ray images is disclosed in EP 0 858 773 A2 and consists of detectors having dimensions similar to those of the detector of an intraoral sensor. The detector system is so constructed that transversal slice acquisition images (TSA images) may be produced and the detector system can be mounted for displacement along its longitudinal axis inside the line detector camera. The detector elements can be displaced along the main axis of the detector by adjustment means.

The sensors used in EP 0 858 773 A2 to produce a PAN or a ceph image typically have an image height of from 135 to 180 mm and an image width of approx. 6 mm. The sensors used to produce TSA images typically have dimensions of about 30×20 mm. The difference in width results from the fact that, in the case of a PAN image, it is desirable for the layer thickness (depth of focus) of the sharp slice to be at least the same as the thickness of the object being imaged, whereas, by contrast, the layer thickness (depth of focus) of the sharp image in the case of a TSA image is about 1 to 3 mm.

An X-ray system for producing images is disclosed in DE 199 41 668 A1. The explanations of the cone beam technology disclosed therein are included herein by reference in their entirety.

However, the production of cone beam images requires, basically, an image detector different from that used for making a tomographic image, which is usually in the form of a CCD sensor operated in TDI mode. The same applies to image detectors that produce individual plane images that are subsequently computed to a tomographic image showing the required depth of focus. CMOS detectors exemplify image detectors of this type.

Although prior art technology already provides for the camera used for the production of a panoramic tomographic image to be unplugged and then replugged for the production of a ceph image, an additional X-ray system is still required to produce a 3D image.

SUMMARY AND OBJECTS OF THE INVENTION

The invention proposes an X-ray system comprising an X-ray sensitive camera for creating tomographic images in which there are means in the camera for the production of images of a subvolume of the jawbone.

The camera is preferably equipped with a primary image detector for producing a panoramic tomographic image and a second image detector for producing a 2D image whilst further means are provided for the production of a plurality of 2D images from different directions and for computation of a 3D image therefrom.

With such an X-ray system it is possible to create both panoramic tomographic images using, for example, a CCD sensor operated in TDI mode, and 3D images of a volume, preferably using cone beam technology and the associated reconstruction algorithms.

The second image detector is advantageously a flat face sensor.

Advantageously, control means are provided which enable imaging of a subvolume containing a portion of the PAN image.

Advantageously, adjustment and/or control means are provided by means of which the camera and the X-ray emitter can be adjusted such that the center of rotation lies within the subvolume to be imaged. To this end, the camera and the X-ray emitter are advantageously mounted on a common support in the manner known in the art in X-ray systems for the production of PAN tomographic images.

According to a further development, adjustment means are provided for the camera and/or the image detector and/or the X-ray emitter and/or the primary diaphragm and/or combinations thereof, and the second image detector can be moved into the radiation path of the X-ray emitter by means of said adjustment means.

Advantageously, adjustment means are provided which cooperate with the camera, which adjustment means can be built into the camera casing or built into connecting means between the camera and the support or mounted on the support itself.

Adjustment means disposed inside the casing are shielded from outside influences. There is relatively more space available when the adjustment means are mounted on the support, and the camera can be made smaller and lighter.

The X-ray system can, in a development, be additionally equipped with a device for the production of ceph images using an additional image detector. When the X-ray emitter is aligned to produce a ceph image, the camera is disposed in the region of the path of radiation between the X-ray emitter and the image detector of the device for the production of the ceph image and in this region the camera is radiolucent.

Alternatively, the path of adjustment can be dimensioned such that when the X-ray emitter is aligned for the purpose of creating teleradiographic images, the camera can be moved outside the path of radiation between the X-ray emitter and the image detector of the device for producing teleradiographic images.

Both methods have the advantage of not requiring manual intervention for switching the imaging method from close-up tomographic images (PAN/3D) to teleradiographic images (ceph images).

Advantageously the camera can be mounted so that it is eccentrically adjustable and can, in a first position, place the image detector in position for creating a PAN tomographic image and, in a second position, place the image detector in position for creating a 3D image. The X-ray fan beam will then impinge on the image detector provided for creating the required image.

An additional object of the invention is the provision of an X-ray sensitive camera consisting of a first X-ray sensitive image detector for the production of a tomographic image. A second X-ray sensitive image detector is provided for the production of plane images.

Such a camera is thus suitable for the production of 3D images as well as for the production of panoramic tomographic images. The present invention makes it possible to create panoramic tomographic images and 3D images with one and the same camera.

Such a camera is thus suitable for the production of different types of X-ray images.

In a first development, both image detectors are mounted in a common casing with the camera. This has the advantage that one interface is sufficient for effecting both mechanical and electrical connections.

The image-detecting active surface of the second image detector can be at least twice as large as the first image detector, in a first dimension. Furthermore, the second image detector may be not more than half as large as the first image detector, in a second dimension. The advantage of this is that, on the one hand, existing elongated line sensors having dimensions suitable for PAN or ceph images and, on the other hand, existing face sensors having the required width for 3D images can be used as image detectors. It is not necessary to provide a PAN sensor having a width sufficient for the production of 3D images, which would cost considerably more than the two individual sensors together.

The second image detector is advantageously mounted alongside the first image detector. The shoulder freedom of the patient to be X-rayed is thus not impaired by the camera.

The second image detector is advantageously mounted on the rear side of the first image detector. Such a camera can be built into traditional X-ray systems for the production of PAN images and thus provide a retrofitting for the production of 3D images, especially if it is possible, for example, to unplug the camera, turn it around relatively to the X-ray emitter, and replug it.

The camera is advantageously designed so that the second image detector can be retrofitted. In this case it is possible to first equip the X-ray system with a camera for the production of PAN images and then, when necessary, install the second image detector in the camera for the production of multilayer images.

According to another development, the second image detector is part of the first image detector or vice versa. On the one hand, this allows the image-detecting surface provided by the second image detector to be used even if no images typical for this type of detector are being produced, and, on the other hand, it allows part of the first image detector to be used for the production of the image using the second image detector.

According to another development, adjustment means are provided to bring either the first or the second image detector, as desired, into alignment with an X-ray emitter for the production of the respective X-ray image.

The adjustment means and both image detectors can be built into a common casing with the camera or on the camera casing and in the region of connecting means for mounting the camera on a support, and the camera in its entirety is then adjustable relatively to said connecting means. In the latter case it is also easy to regulate positioning of the camera visually from outside and confirm that the correct sensor has been moved into the proper position for creation of the image. Furthermore, the camera casing can be kept more compact than when the sensor adjustment means are disposed only within the camera casing.

If the camera has a radiolucent region, it is possible to leave the camera in the X-ray fan beam for the creation of an additional image without any significant negative impact on the image production. The camera can therefore remain in place and need not be removed.

According to a development, the radiolucent region is located between the first and second image detectors.

According to another development, the radiolucent region is located adjacent to the first and second image detectors.

BRIEF DESCRIPTION OF THE DRAWINGS

An exemplary embodiment of the invention is illustrated in the drawings, in which.

DETAILED DESCRIPTION OF EXEMPLARY EMBODIMENTS OF THE INVENTION

Figure 1A:
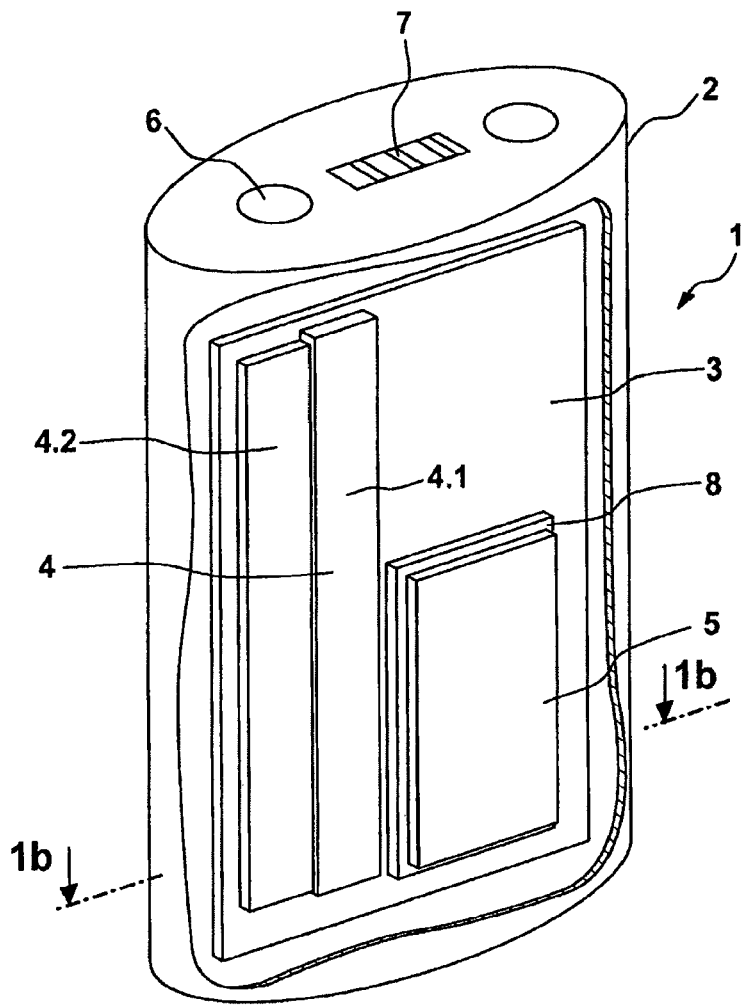
FIGS. 1a and 1b show a camera with two different image detectors located adjacent to each other.

A camera 1 of the invention is illustrated in FIG. 1a in a perspective view. Camera 1 has a casing 2 in which a circuit board 3 is installed. A first image detector 4 in the form of a line sensor is provided on circuit board 3, which detector is a CCD sensor in this exemplary embodiment and has a length which is many times greater than its width. The first image detector 4 can be divided into an image detecting area in the form of a CCD sensor 4.1 and read-out electronics 4.2.

Such forms of an image detector are well known in the prior art. In principle, image detectors such as CMOS sensors that produce individual images in the form of a plane image can also be used.

Adjacent to the first image detector 4 there is provided an second image detector 5, which is constructed in the form of a face sensor and from which full frames can be read out at high speed. This second image detector 5 is also mounted on circuit board 3, of which the spatial dimensions are, for example, 60 mm×60 mm (height×width) or approximately 60 mm×80 mm, so that the image detector can also be mounted more or less transversely. It has been found that a subvolume of 60 mm×60 mm×60 mm is sufficient to adequately record the areas to be imaged. The exact dimensions must be chosen so that the dimensions of the subvolume to be imaged are covered.

Casing 2 is equipped with mechanical and electrical connecting means 6, 7 so that camera 1 can be mounted on a standard support structure (not shown).

Figure 1B:
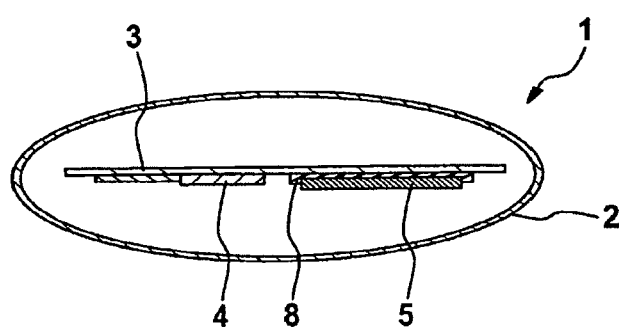

A cross section through the camera 1 taken along the line 1b-1b in FIG. 1a is illustrated in FIG. 1b. Circuit board 3 with the first image detector 4 and the second image detector 5 is shown in casing 2, and the second image detector 5 is installed in a holding device 8 on circuit board 3.

Figure 2A:
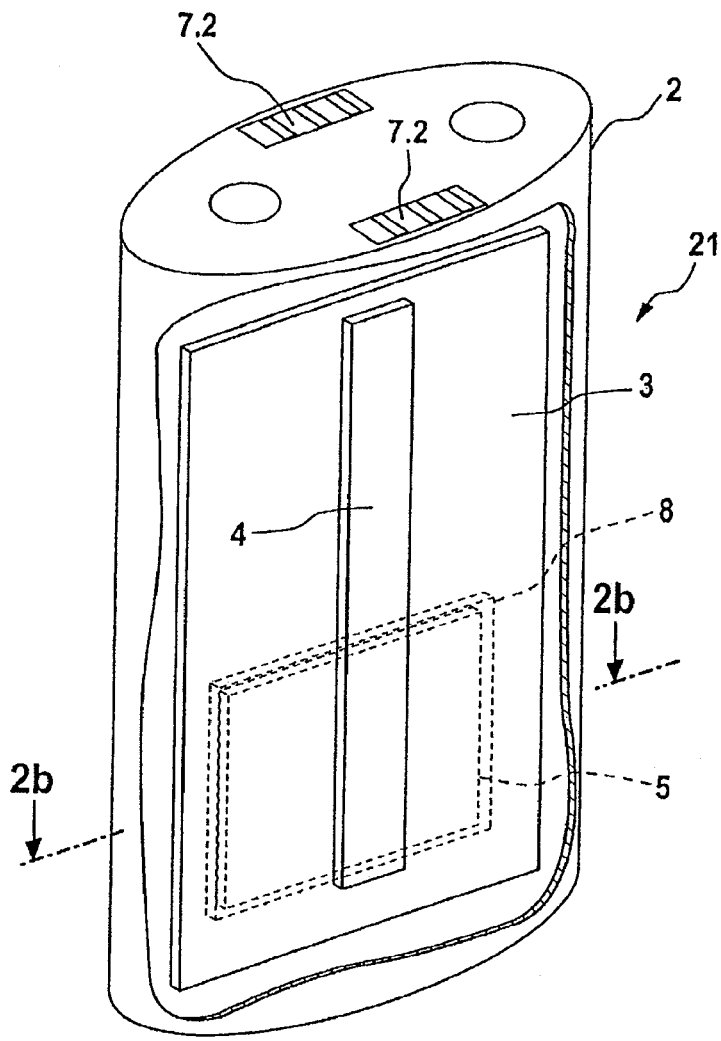
FIGS. 2a and 2b show a camera with two different sensors that are oriented back to back.

FIG. 2a shows a camera 21, which likewise has a casing 2 and a circuit board 3, and the first image detector 4 is mounted on the circuit board 3. The second image detector 5, represented by dashed lines, is mounted on the rear side of circuit board 3.

In order to preserve electrical contact when the camera 21 is rotated, the electrical contact 7 of the embodiment illustrated in FIG. 1a is duplicated as electrical contacts 7.1 and 7.2 in the embodiment illustrated in FIG. 2a. This double contact can obviously also be provided on means (not shown) for coupling the camera to an X-ray system.

Figure 5:
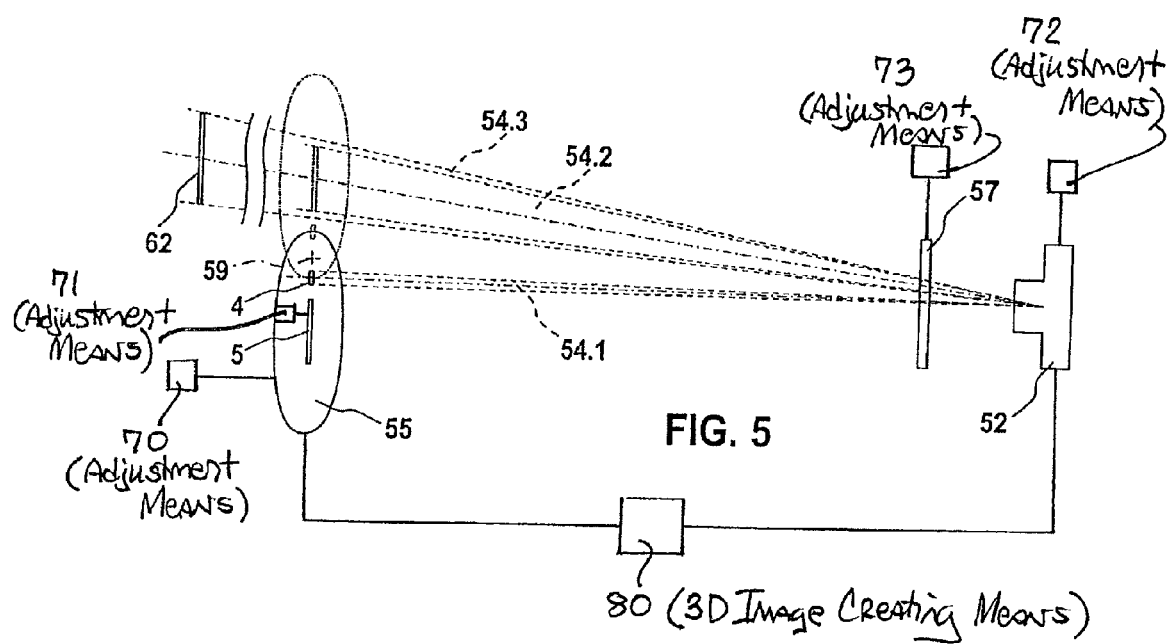
FIG. 5 is a further diagram illustrating an eccentrically positioned camera.

When the camera is rotated as in FIG. 5, a connection that can be unplugged is not required. This rotation can be achieved by a motor or manually.

Figure 2B:
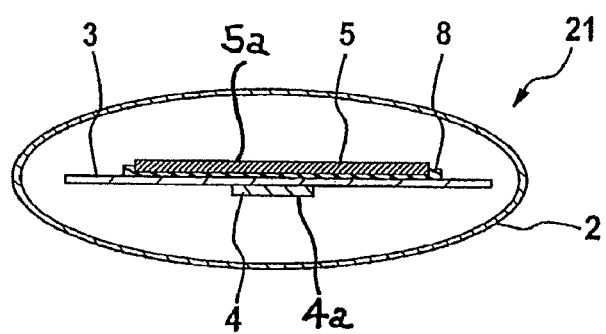

The cross-sectional illustration of FIG. 2b clearly shows the back-to-back arrangement of the two image detectors 4, 5, that is, on either side of circuit board 3. Image detector 5 is installed in the holding device 8. The X-ray sensitive surfaces 4a, 5a thereof face in opposite directions.

Since an X-ray system for the production of a PAN image will be considered to be the basic device on account of the fact that such images are produced more frequently, the camera 1 or 21 can be designed so that the image detector 5 for the 3D image can be retrofitted. Retrofitting can be carried out, for example, by opening the casing and plugging in the image detector 5 in an appropriate place, for example, in the holding device 8, and making any additional necessary electrical or mechanical connections.

Prior art X-ray systems for the production of panoramic tomographic images have fixed connecting means between the X-ray emitter on the one hand and the detector on the other hand so that both components are moved together as a unit. As a rule, the detector as such is fastened rigidly to the common support together with the X-ray emitter.

Figure 3A:
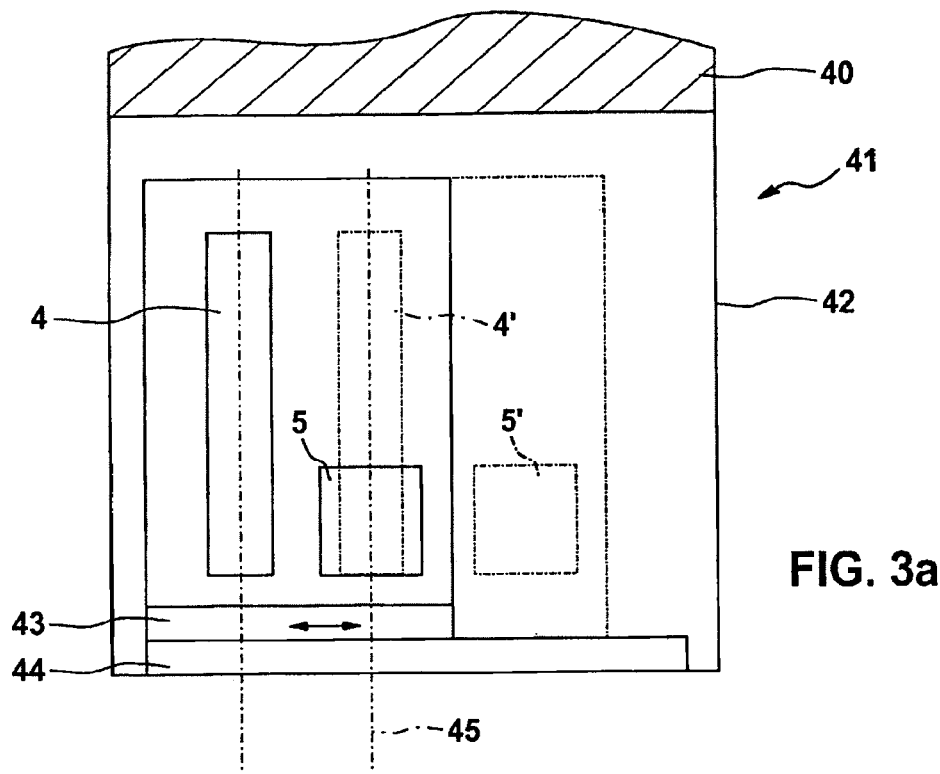
FIGS. 3a and 3b show a first and second adjustment mechanism for displacing the sensors inside a camera casing and for displacing the camera casing respectively.
Figure 3B:
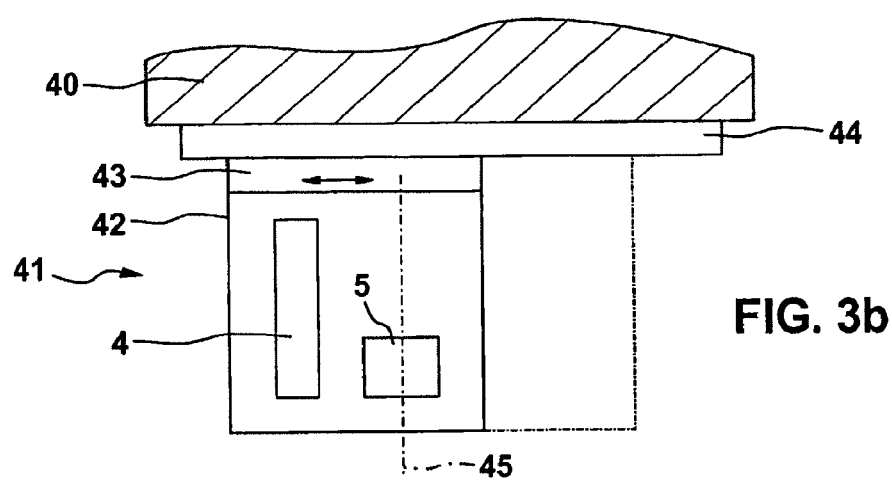

A first and second adjustment mechanism for positioning the image detectors are illustrated in FIGS. 3a and 3b.

A camera 41 is shown, which is attached to a support structure 40 and has a casing 42 in which the image detectors 4, 5 are guided by an adjustment mechanism in the form of a carriage 43 on a guide track 44. The image detectors 4, 5 can thus be moved with the carriage 43 the guide track 44 from the position illustrated to the dashed line position 4', 5', so that instead of the face sensor of the image detector 5, the line detector of image detector 4 moves into the X-ray fan beam represented by the line 45.

In FIG. 3b, the adjustment mechanism is located between a camera 41 and the support structure 40. Camera 41 is mounted via its casing 42 on the support structure 40 for displacement thereon, as represented by carriage 43 attached to the camera 41 and the guide track 44 attached to the support structure 40. This allows the entire camera 41 to be moved from the position illustrated to the position represented by the dashed line, so that the X-ray beam, again illustrated by line 45, is aligned not with image detector 5 but with image detector 4.

Camera 41 is attached by connecting means and the connecting means can also include adjustment means.

Alternatively, an image can be produced with a motor-driven camera holder, in which the sensor is positioned according to the desired mode of operation. The motor-driven camera holder forms the connection between the connecting means of the camera and the support. Said holder can be designed so that the camera plus connecting means can be moved along a guide track or pivoted by means of a pivoting mechanism. Thus the camera can be moved automatically into the optimal position in the system. A direct image series for a PAN image followed by a multilayer image can be produced in this manner without any additional intervention on the part of the operator.

Figure 4A:
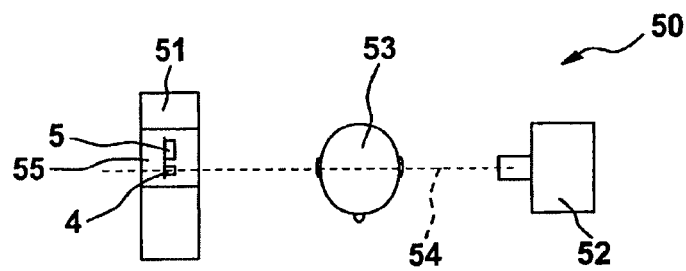
FIG. 4a shows a diagram of an X-ray system of the invention for the production of PAN and TSA images in a first imaging situation (PAN)

The main parts of an X-ray system 50 are illustrated in FIG. 4a, specifically an imaging device with an imaging unit 51 and an X-ray emitter 52, in which the object to be examined in the form of a patient's head 53 is positioned between the X-ray emitter 52 and the imaging unit 51. For the production of a panoramic tomographic image, the X-ray beam 54 emitted from the X-ray emitter 52 is directed to the image detector 4 constructed in the form of a line detector, so that the required length for producing a PAN image of the upper and lower jawbones is provided.

Meanwhile, the image detector 5 in the form of a face sensor is in a neutral position outside the X-ray beam 54.

Figure 4B:
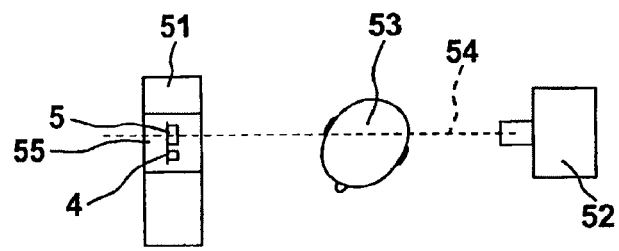
FIG. 4b shows the X-ray system of FIG. 4a in a second imaging position (TSA)

An imaging situation for producing a 3D image of a specific subregion of the jawbone of the patient's head 53, such as a single tooth, is illustrated in FIG. 4b. The camera 55 disposed on the imaging unit 51 is now aligned so that the image detector 5 is exposed to the X-ray beam 54, and the image detector 4 is now in a neutral position. Accordingly, in the case of a camera 55 having a sensor configuration as in FIGS. 2a and 2b, either the image detector 4 or the image detector 5 will be oriented toward the X-ray emitter 52. For this purpose, the camera 55 can either be unplugged and replugged or automatically rotated by a motorized adjustment mechanism.

Obvious to the person skilled in the art, but not always illustrated in the figures, is the use of a primary diaphragm with mechanically rigid default orifices or an orifice that can be regulated by moveable beam-delimiting elements (not shown) for restricting the extent of the X-ray beam 54, the extent of the X-ray beam 54 being such that it substantially matches the image-sensitive area of the image detector 4 or 5 or even perfectly fits the image-sensitive surfaces of the image detectors 4 and 5 respectively, in accordance with the relevant standards. Radiation bombardment by X-rays not needed for the production of the image is thus avoided.

Figure 4C:
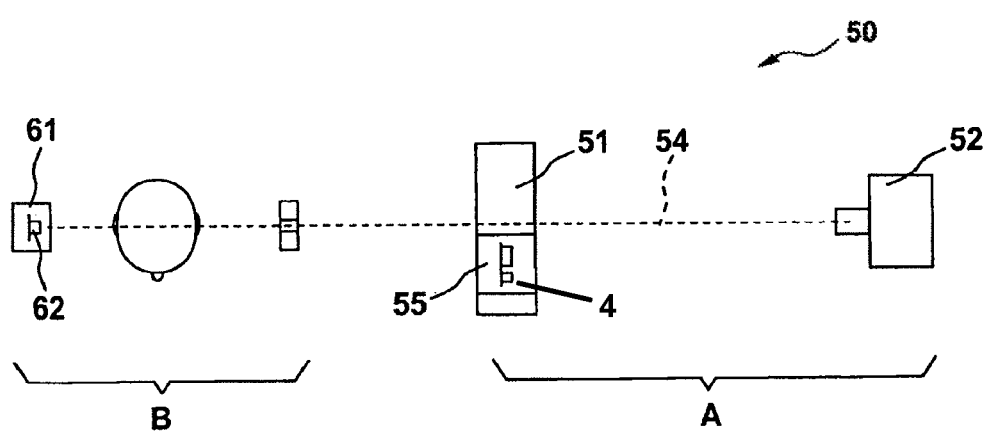
FIG. 4c shows an additional X-ray system having a third imaging position (ceph)

A diagram illustrating the production of a ceph image is shown in FIG. 4c.

A ceph image can be produced in an X-ray system 50 equipped with a PAN unit "A" and a ceph unit "B" by bringing a separate camera 61, equipped with an image detector 62 with a line sensor of appropriate length for the production of the ceph image, into the ceph position. The camera 55 for the production of the PAN image and the 3D image is positioned so that the X-ray beam 54 emitted from the X-ray emitter 52 is directed past the casing of said camera 55.

If a separate ceph sensor is not used, the first camera 55 can be unplugged and replugged manually if the image detector 4 for the production of the PAN image located therein is also long enough to fit the dimensions required to produce the ceph image.

Figure 4D:
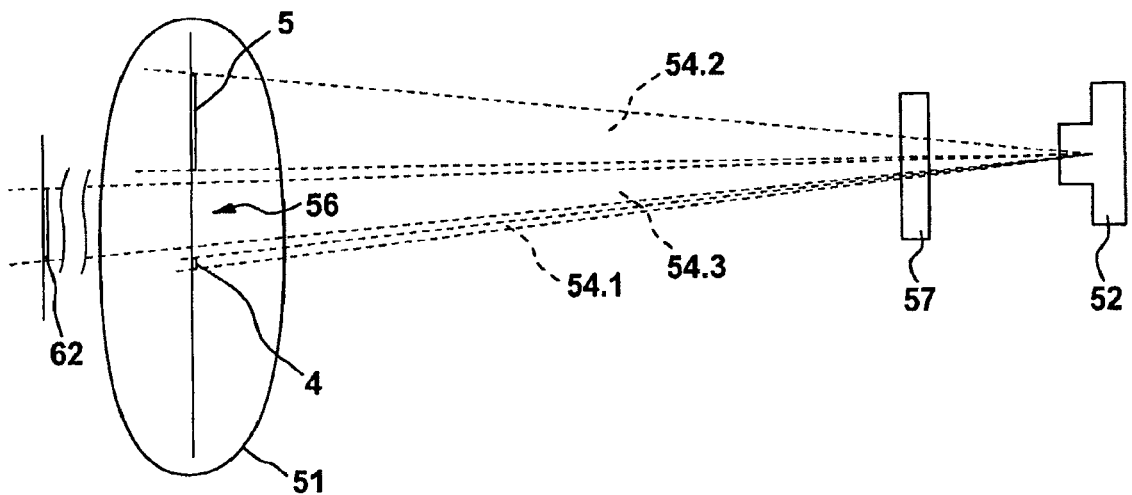
FIG. 4d shows an additional X-ray system having an adjustable primary diaphragm for three imaging positions.

A camera 55 in which there is a radiolucent zone 56 between the two image detectors 4, 5 is illustrated in FIG. 4d. The dimensions of the radiolucent zone 56 are such that a fan beam 54 emitted by X-ray emitter 52 can pass substantially unhindered through the camera 51.

The camera 55 is stationary in this exemplary embodiment and the fan beam 54.1-54.3 is aimed at the appropriate image detector 4, 5, 62 by an adjustable primary diaphragm 57. To this end, the geometric dimensions of the primary diaphragm 57 are adjusted to the size of the image to be produced. The width required for the production of a PAN image is, say, 0.9 mm.

Figure 4E:
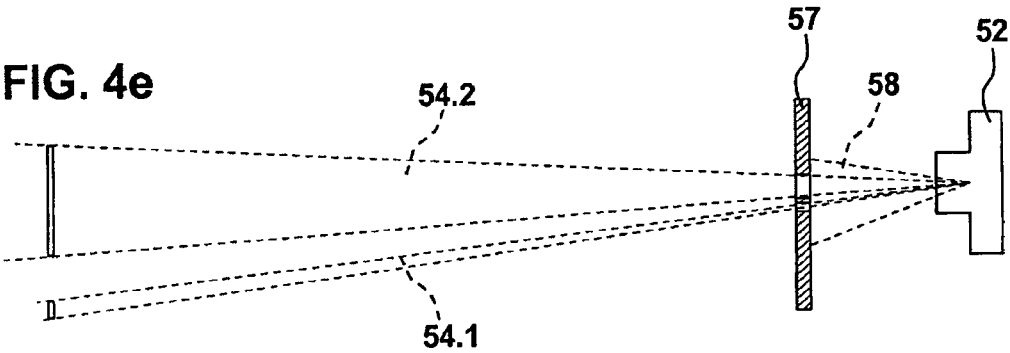
FIGS. 4e and 4f are diagrams illustrating various imaging situations.

This principle is illustrated in detail in FIG. 4e. The primary diaphragm 57 here has two orifices that allow the passage of the appropriate fan beam 54.1, 54.2 for producing the different types of image. The other fan beam is obviously blocked during the production of an image. The cone of radiation 58 produced by the X-ray emitter 52 is sufficiently large to provide the desired fan beam 54.1, 54.2 or, when needed, the fan beam for a teleradiographic image.

Figure 4F:
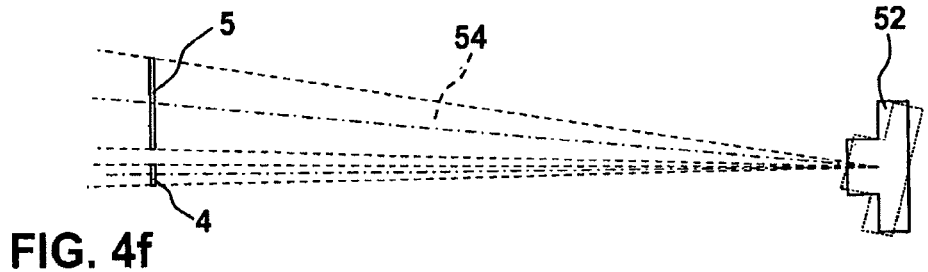

In lieu of splitting the fan beam 58 emitted from the X-ray emitter 52 by a variable primary diaphragm 57, the X-ray emitter 52 can, if desired, be directed, by adjustment mechanisms, toward either one of the image detectors 4, 5, as illustrated in FIG. 4f. Such an adjustment is already known for combined PAN/ceph devices. The adjustment may be achieved by sliding or, as illustrated, by pivoting. The advantage gained in this case is that the central ray of the X-ray fan beam 58 always lies within the fan beam 54.

With the eccentric mounting of the camera 55 illustrated in FIG. 5, a PAN image can be produced in an initial alignment of the camera 55 in which the image detector 4 lies within the X-ray fan beam 54.1. With this alignment of camera 55 it is also possible to produce a ceph image, as the X-ray fan beam 54.3 is directed past camera 55 to image detector 62. A 3D image can be produced when camera 55 is in the position represented by the dashed lines, which is achieved by rotating it about the center of eccentricity 59. In doing so, the image detector 5 is positioned closer to the X-ray fan beam 54.3 for the ceph image than the image detector 4. An adjustment means 70 is connected to the camera 55 for movement of the camera 55 relative to the fan beam 54.1, an adjustment means 71 is connected to the second image detector 5 for movement thereof within the camera 55, an adjustment means 72 is connected to move the X-ray emitter 52, an adjustment means 73 is connected to the primary diaphragm 57 for movement thereof relative to the fan beam 54, and a means 80 is connected to the camera 55 and the X-ray emitter 52 to create 3D images from several 2D images from different directions using cone beam technology with reconstruction algorithms.

The arrangement illustrated has the advantage that a short jib for the ceph camera is sufficient for producing the ceph image, because the X-ray fan beam 54.3 stays close to the wall.

The following fundamental principle must be observed: a different primary diaphragm will be used for the production of a PAN image, a 3D image, and a ceph image respectively and each image will be created using only one imaging method. When several X-ray fan beams are illustrated together in the exemplary embodiments, this serves merely to clarify the geometric relationships. The primary diaphragm, however, is constructed and adjusted such that the desired image detector is activated by the correct X-ray fan beam for producing the desired image.

What is claimed is:

1. An X-ray system comprising:
    an X-ray sensitive camera and an X-ray emitter, the X-ray sensitive camera comprising:
        a first image detector that forms at least one panoramic image, the first image detector having an X-ray sensitive surface that detects first X-rays emitted by the X-ray emitter; and
        a second image detector that forms at least one two-dimensional image, the second image detector having an X-ray sensitive surface that detects second X-rays emitted by the X-ray emitter, wherein
        the first image detector and the second image detector are arranged such that the X-ray sensitive surface of the first image detector faces an opposite direction from the X-ray sensitive surface of the second image detector, and
        the first image detector and the second image detector are positionable relative to the X-ray emitter.

2. The X-ray system according to claim 1, wherein the X-ray sensitive surface of the second image detector detects the second X-ray images and outputs signals for forming the at least one two-dimensional image.

3. The X-ray system according to claim 1, wherein the X-ray sensitive camera comprises an adjuster arranged to position at least one of the first and second image detectors in a selected orientation relative to the X-ray emitter.

4. The X-ray system according to claim 1, wherein the X-ray sensitive camera comprises a housing enclosing the first and second X-ray detectors.

5. The X-ray system according to claim 1, wherein the X-ray sensitive camera comprises a circuit board disposed between the first image detector and the second image detector.

6. The X-ray system according to claim 1, wherein
    the X-ray sensitive camera is mounted for eccentric displacement such that, in a first position, the first image detector is positioned in an X-ray beam emitted by the X-ray emitter to create at least one panoramic tomographic image, and, in a second position, the second image detector is positioned in the X-ray beam to create the at least one two-dimensional image.

7. The X-ray system according to claim 6, wherein the X-ray sensitive camera comprises a housing enclosing the first image detector and the second image detector, and an adjuster arranged to position the first image detector and the second image detector relative to the X-ray emitter by rotating the housing about a predetermined axis.

8. The X-ray system according to claim 1, further comprising a device for producing teleradiographic images.

9. The X-ray system according to claim 8, wherein the X-ray sensitive camera comprises a radiolucent zone between the first image detector and the second image detector such that an X-ray beam emitted by the X-ray emitter passes through the radiolucent zone substantially unhindered.

10. The X-ray system according to claim 1, further comprising a device that computes a three-dimensional image using a plurality of two-dimensional images from a plurality of directions.

\* \* \* \* \*